US00PP10353P

United States Patent [19]

Larsen

[11] Patent Number: Plant 10,353

[45] Date of Patent: Apr. 28, 1998

[54] OSTEOSPERMUM PLANT NAMED 'SUNNY LADY'

[75] Inventor: Bjarne Larsen, Odense, Denmark

[73] Assignee: Paul Ecke Ranch, Encinitas, Calif.

[21] Appl. No.: 698,336

[22] Filed: Aug. 15, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV-ROM Plant Variety Database 'Sunny Lady', Osteospermum, PBR OST 0005, 1992.

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Sunny Lady', particularly characterized by its preading growth habit with excellent dark purple flower color, early flowering, glossy green foliage, and suitability to 6 inch pots, and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Sunny Lady', and was developed by the inventor Bjarne Larsen in Odense, Denmark in 1990 by crossing two cultivars of unknown origin. Both cultivars are proprietary to the breeding program.

Asexual reproduction by terminal (stem tip) cuttings taken by me or under my supervision at Kernen Greenhouse in Odense, Denmark, has shown that the unique features of this new Osteospermum are stabilized and are reproduced true to type in successive propagations.

The folowing characteristics distinguish the new Osteospermum from both its parent varieties and other cultivars of this general type known and used in the floriculture industry:

1. A unique dark purple flower color.
2. A spreading compact growth habit.
3. Mid-season flower response.
4. Well suited for 6" pots, nursery containers, and hanging baskets.

'Sunny Lady' is similar to the unpatented cultivar 'Tivoli'. The growth habit of 'Sunny Lady' is more upright, flower petioles are shorter, and plant structure is less coarse. 'Sunny Lady', is also similar to the unpatented cultivar 'James Elliman' in ray flower coloring, but is distinctly different by the lack of white markings on the ray floret.

Plant comparisons shown in Chart A for 'Cape Daisy Lusaka', a plant described and illustrated in co-pending U.S. patent application Ser. No. 08/695,392, and 'Sunny Lady' are described as one hanging basket containing 3 plants.

CHART A

| Characteristic | 'Cape Daisy Lusaka' | 'Sunny Lady' |
|---|---|---|
| Plant Height (above the pot) | 47 cm | 33 cm |
| Plant Width | 61 cm | 65 cm |
| Weeks to Flower | 8 | 8 |
| Flower Head Diameter | 7.8 cm | 7.5 cm |
| Flower Color - upper surface mature ray florets | RHS 78B and Near RHS 78C | RHS 78A and 78C |

Immature flowers of 'Cape Daisy Lusaka' are light purple near R.H.S. 75B on opening and change to a medium purple at maturity. Flowers of 'Sunny Lady' are a medium purple on opening and darken only slightly at maturity.

DESCRIPTION OF PHOTOGRAPH

The accompanying colored photograph is a side perspective view of the new cultivar, showing color as true as it is reasonably possible to obtain in a colored reproduction of this type.

DESCRIPTION OF THE PLANT

The following is a detailed description of my new Osteospermum cultivar based on plants grown under commerial practice in Encinitas, Calif. Three rooted cuttings were transplanted into 26 cm (10 inch) hanging baskets on Dec. 11, 1995. Plants were pinched on Jan. 2, 1996, and received plant growth regulator on Jan. 16 and 31. The values, measurements and observations noted below were taken from plants in bloom on Feb. 29, 1996, and continued in flower through April 1996.

On Apr. 9, 1996, I observed a plant in a 26 cm hanging basket 33 cm tall. This basket had three branched plants with an overall height of 45 cm and an overall width of 65 cm. Each plant had 5 strong branches, originating from within 1.5 cm of the soil line, for a total of 15 branches. Each primary branch was approximately 12 cm long terminating in a flower. At observation, there were 31 flowers open and 90 flower buds in various stages of development. Three secondary shoots subtend the terminal flower from the top 3 nodes on the primary shoot. These secondary shoots measured 21 to 27 cm and terminated in a flower.

Color references are made to The Royal Horticultural Society Colour Chart (R.H.S.), except where general terms of ordinary dictionary significance are used.

THE PLANT

Origin: Seedling from cross pollination.

Parentage: Cross between seed parent of unknown origin and pollen parent of unknown origin.

Classification:

*Botanical.—Osteospermum ecklonis.*

*Comman name.*—Osteospermum.

*Cultivar name.*—'Sunny Lady'

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

D. *Growth retardant application.*—Standard growth retardant applications include 1–2 applications of daminozide/butanedioic acid mono (2.2 dimethylhydrazide) at a rate of 2,500 ppm. Applications are made as foliar sprays. Growth retarding chemicals generally reduce plant height ⅓.

Plant description:

A. *Form.*—Symmetrical, low growing perennial shrub, with good branching characteristics after pinching, giving the plant a full appearance.

B. *Habit of growth.*—Vigorous, spreading habit, producing approximately 12 leaves per stem and terminating in flowers. After the initial flower is formed, typically 3 subordinate axillary shoots develop from the uppermost leaves producing additional flowering shoots. This process is continuous so long as night temperatures remain below 16° C.

C. *Foliage description*—1. Leaf shape: Obovate with acuminate tip and attenuate leaf base. 2. Leaf blade size: Mature leaves 7–9 cm long and 3–4 cm wide. 3. Petiole length: Approximately 2.5–3 cm in length. 4. Leaf Margin: Slightly sunuate with 3 to 5 pointed lobes on either side of the leaf blade. 5. Leaf texture: Slightly undulant and twisted at the tip. i) Upper surface: Slightly pubescent with short, white trichomes evenly distributed throughout the leaf surface. ii) Under surface: Glabrous. 6. Leaf color: Dark green. i) Upper surface: Near R.H.S. 147A-B. ii) Under surface: Near R.H.S. 146A. 7. Venation: Palmately branched with a predominate light green colored mid-vein on the upper surface. 8. Foliage fragrance: Characteristic Osteospermum plant fragrance, particularly notable when foliage is wet.

Inflorescence description: Daisy type composite flower with disk and ray florets that close at night and open in the morning. Florets on the flower heads are imperfect with pistillate ray florets and staminate disk florets.

A. *Flowering habits.*—Flowering is determinate with one primary flower at the end of a long (11–14 cm) pedicel on open flower. Each pedicel had approximately 10 leaflets on end of the pedicel. A secondary flower arises from the base of the primary pedicel.

B. *Natural flowering season.*—Flowering occurs primarily February through October in the northern hemisphere. Initiation occurs after a cool temperature vernalization (10°–17° C.). Floriferousness may wane during hot summer days in temperate climates. Plants are initially potted using rooted cuttings, pinched 2 weeks later, than maintained at a temperature of 10°–12° C. for 4 weeks and thereafter grown for 7 weeks at a temperature of 18° C., for a total growing time to flower of 15 weeks.

C. *Flower buds.*—Flower buds develop successively on secondary branches, reaching a size of 2 cm long and 1 cm wide prior to opening.

D. *Flowers borne.*—Singularly 10–12 cm above the plant canopy.

E. *Quantity of flowers.*—Secondary flowers occur progressively around the primary flower so that tight buds to mature flowers are visible at the same time.

F. *Flower head.*— 1. Number of florets: 20–22 ray florets and numerous disk florets, making up a flower disk approximately 1.2 cm in diameter. 2. Shape: Narrow linear florets with obtuse to acute tips and acute bases. Florets approximately 3.2 cm long and 0.8 cm. wide. 3. Color: Ray florets are bright purple; disk florets are purplish-red. i) Upper surface of ray florets; Alternating stripes near R.H.S. 78A and 78C. ii) Under surface of ray florets; Alternating stripes near R.H.S. 83B and 84C. iii) Disk florets: Near R.H.S. 86A. 4. Surface: i) Upper surface of ray florets: Glabrous. ii) Under surface of ray florets: Glabrous but pubescent near the base. 5. Inflorescence size: Up to 7.5 cm in diameter. 6. Flower fragrance: None.

*Reproductive organs.*—1. Stamens: Short stamens emerge on outermost disk florets and progress toward the center. 2. Anther: Each disk floret has 1 stamen terminating in a 5-part anther. 3. 1 Pollen: Copious and golden yellow. 4. Stigma: Bipartite. 5. Styles: Short, approximately 2–3 mm long and purple. 6. Ovary: Inferior to florets and green in color.

H. *Resistance.*—1. Frost: Withstands light frost. 2. Root, stem, foliage and flower diseases: Highly resistant.

What is claimed is:

1. A new and distinct cultivar of Osteospermum plant named 'Sunny Lady' as illustrated and described.

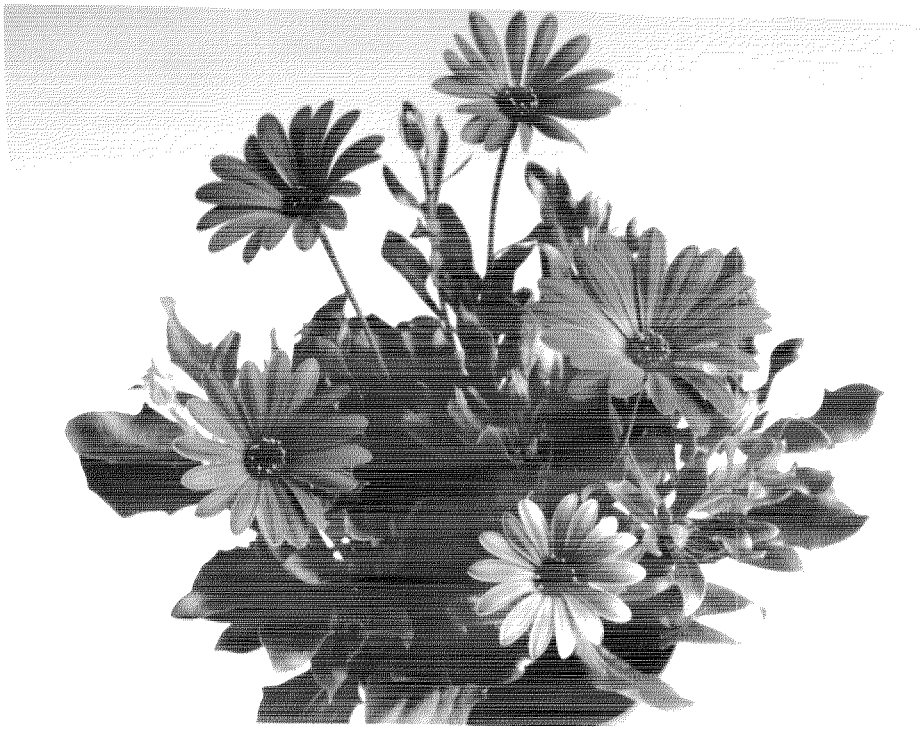

* * * * *